US008858764B2

(12) United States Patent
Peng et al.

(10) Patent No.: US 8,858,764 B2
(45) Date of Patent: Oct. 14, 2014

(54) ELECTRON BEAM SCULPTING OF TUNNELING JUNCTION FOR NANOPORE DNA SEQUENCING

(75) Inventors: Hongbo Peng, Chappaqua, NY (US); Stephen M. Rossnagel, Pleasantville, NY (US); Ajay K. Royyuru, Congers, NY (US); Gustavo A. Stolovitzky, Riverdale, NY (US); Deqiang Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/606,815

(22) Filed: Sep. 7, 2012

(65) Prior Publication Data

US 2012/0325656 A1    Dec. 27, 2012

Related U.S. Application Data

(63) Continuation of application No. 13/359,729, filed on Jan. 27, 2012.

(60) Provisional application No. 61/437,102, filed on Jan. 28, 2011.

(51) Int. Cl.
  *H01L 21/00* (2006.01)
  *G01N 33/487* (2006.01)

(52) U.S. Cl.
  CPC ....... *G01N 33/48721* (2013.01); *Y10S 977/712* (2013.01)
  USPC ...................................... 204/229.8; 977/712

(58) Field of Classification Search
  USPC ................. 204/450, 479, 471, 518, 600, 547; 977/707, 712, 780, 962, 742, 847, 890; 435/6.1, 7.1; 216/19
  See application file for complete search history.

(56) References Cited

U.S. PATENT DOCUMENTS

| 4,576,829 A | 3/1986 | Kaganowicz et al. |
| 4,692,992 A | 9/1987 | Hsu |

(Continued)

FOREIGN PATENT DOCUMENTS

| EP | 0261592 A1 | 9/1987 |
| EP | 1441213 | 7/2004 |

(Continued)

OTHER PUBLICATIONS

G. Sigalov, et al. "Detection of DNA Sequences Using an Alternating Electric Field in a Nanopore Capacitor", Nano Letters, vol. 8, No. 1, 2008, p. 56-63.*

(Continued)

*Primary Examiner* — J. Christopher Ball
(74) *Attorney, Agent, or Firm* — Cantor Colburn LLP; Vazken Alexanian

(57) ABSTRACT

A technique for a nanodevice is provided that includes a reservoir filled with a conductive fluid and a membrane separating the reservoir. The membrane includes an electrode layer having a tunneling junction formed therein. A nanopore is formed through the membrane, and the nanopore is formed through other layers of the membrane such that the nanopore is aligned with the tunneling junction of the electrode layer. When a voltage is applied to the electrode layer, a tunneling current is generated by a base in the tunneling junction to be measured as a signature for distinguishing the base. When an organic coating is formed on an inside surface of the tunneling junction, transient bonds are formed between the electrode layer and the base.

7 Claims, 14 Drawing Sheets

(56) References Cited

U.S. PATENT DOCUMENTS

| | | | |
|---|---|---|---|
| 5,671,086 | A | 9/1997 | Parvin et al. |
| 6,180,490 | B1 | 1/2001 | Vassiliev et al. |
| 6,217,872 | B1 | 4/2001 | Okayama et al. |
| 6,413,792 | B1 | 7/2002 | Sauer et al. |
| 6,582,926 | B1 | 6/2003 | Chilkoti |
| 6,621,191 | B1 | 9/2003 | Nomura et al. |
| 6,627,067 | B1 | 9/2003 | Branton et al. |
| 6,727,174 | B1 | 4/2004 | Kotecki et al. |
| 6,777,260 | B1 | 8/2004 | Chen |
| 6,962,849 | B1 | 11/2005 | Kamal et al. |
| 7,282,130 | B2 | 10/2007 | Flory |
| 7,347,921 | B2 | 3/2008 | Barth et al. |
| 7,351,648 | B2 | 4/2008 | Furukawa et al. |
| 7,468,271 | B2 | 12/2008 | Golovchenko et al. |
| 7,540,717 | B2 | 6/2009 | Sheng et al. |
| 7,553,730 | B2 | 6/2009 | Barth et al. |
| 7,560,141 | B1 | 7/2009 | Kim et al. |
| 7,846,738 | B2 | 12/2010 | Golovchenko et al. |
| 2005/0019784 | A1 | 1/2005 | Su et al. |
| 2005/0026238 | A1 | 2/2005 | Berndt |
| 2005/0101100 | A1 | 5/2005 | Kretchmer et al. |
| 2005/0110990 | A1 | 5/2005 | Koo et al. |
| 2005/0158763 | A1 | 7/2005 | Ivanisevic et al. |
| 2006/0105553 | A1 | 5/2006 | Wellhausen |
| 2006/0154399 | A1 | 7/2006 | Sauer et al. |
| 2006/0169588 | A1 | 8/2006 | Jacobson et al. |
| 2006/0180469 | A1 | 8/2006 | Han et al. |
| 2006/0246497 | A1 | 11/2006 | Huang et al. |
| 2007/0020146 | A1 | 1/2007 | Young et al. |
| 2007/0042366 | A1 | 2/2007 | Ling |
| 2007/0048745 | A1 | 3/2007 | Joyce et al. |
| 2007/0138132 | A1 | 6/2007 | Barth |
| 2007/0187694 | A1 | 8/2007 | Pfeiffer |
| 2007/0190542 | A1 | 8/2007 | Ling et al. |
| 2008/0003571 | A1 | 1/2008 | McKernan et al. |
| 2008/0032290 | A1 | 2/2008 | Young |
| 2008/0102504 | A1 | 5/2008 | Akeson et al. |
| 2008/0119366 | A1 | 5/2008 | Sauer et al. |
| 2008/0171316 | A1 | 7/2008 | Golovchenko et al. |
| 2008/0187915 | A1 | 8/2008 | Polonsky et al. |
| 2008/0257859 | A1 | 10/2008 | Golovchenko et al. |
| 2009/0136958 | A1 | 5/2009 | Gershow et al. |
| 2009/0188794 | A1 | 7/2009 | Simon et al. |
| 2009/0221443 | A1 | 9/2009 | Heller et al. |
| 2009/0222216 | A1 | 9/2009 | Hibbs et al. |
| 2010/0025249 | A1 | 2/2010 | Polonsky et al. |
| 2010/0084276 | A1 | 4/2010 | Lindsay |
| 2010/0327255 | A1 | 12/2010 | Peng et al. |
| 2010/0327847 | A1 | 12/2010 | Leiber et al. |
| 2010/0331194 | A1 | 12/2010 | Turner et al. |
| 2011/0052813 | A1 | 3/2011 | Ho et al. |
| 2011/0085759 | A1 | 4/2011 | Lee et al. |
| 2011/0174629 | A1* | 7/2011 | Bouchet et al. ............... 205/131 |
| 2011/0220574 | A1 | 9/2011 | Bakajin et al. |
| 2011/0236984 | A1 | 9/2011 | Sun et al. |
| 2011/0279125 | A1 | 11/2011 | Bedell et al. |
| 2012/0146162 | A1 | 6/2012 | Cho et al. |
| 2012/0193235 | A1 | 8/2012 | Afzali-Ardakani et al. |
| 2012/0193236 | A1 | 8/2012 | Peng et al. |
| 2012/0193237 | A1 | 8/2012 | Afzali-Ardakani et al. |
| 2013/0037410 | A1 | 2/2013 | Xu et al. |
| 2013/0203050 | A1 | 8/2013 | Huber; Martin; et al. |

FOREIGN PATENT DOCUMENTS

| | | |
|---|---|---|
| EP | 1486775 A | 12/2004 |
| WO | WO0181908 A | 11/2001 |
| WO | WO2006122317 | 11/2006 |
| WO | WO2007084163 A | 7/2007 |
| WO | WO2008051308 A2 | 5/2008 |
| WO | WO2008132643 A1 | 11/2008 |
| WO | WO 2009020682 A2 * | 2/2009 |
| WO | WO2009032756 A2 | 3/2009 |
| WO | WO 2009/109727 * | 9/2009 |

OTHER PUBLICATIONS

U.S. Appl. No. 12/820,543, filed Jun. 22, 2012; First Named Inventor: Ali Afzali-Ardakani.

U.S. Appl. No. 13/248,176; Title: Selective Placement of Carbon Nanotubes via Coulombic Attraction of Oppositely Charged Carbon Nonotubes and Self-Assembled Monolayers; filed Sep. 29, 2011; First Named Inventor: Ali Afzali-Ardakani.

Hongbo Peng, et al., pending U.S. Appl. No. 13/359,729, entitled "Electron Beam Sculpting of Tunneling Junction for Nanopore DNA Sequencing," filed Jan. 27, 2012.

Hongbo Peng, et al., pend U.S. Appl. No. 13/359,743, entitled "DNA Motion Control Based on Nanopore with Organic Coating Forming Transient Bonding to DNA," filed Jan. 27, 2012.

Hongbo Peng, et al., pending U.S. Appl. No. 13/359,750, entitled "DNA Sequencing Using Multiple Metal Layer Structure with Organic Coatings Transient Bonding to DNA Bases," filed Jan. 27, 2012.

Hong Peng, et al., pending U.S. Appl. No. 13/359,766, entitled "DNA Sequencing Using Multiple Metal Layer Structure with Different Organic Coatings Forming Different Transient Bondings to DNA," filed Jan. 27, 2012.

A. Bergvall et al., "Graphene nanogap for gate-tunable quantum-coherent single-molecule electronics," Phys. Rev. B, vol. 84, No. 15, 2011, 155451, 7 pages.

A. J. Storm et al., "Fabrication of solid-state nanopores with single-nanometre precision," Nature Materials, vol. 2, Aug. 2003, pp. 537-540.

R. Akeson M., Branton D., Kasianowicz J., Brandin E. and Deamer D.W., "Microsecond Timescale Discrimination Among Polysytidylic Acid, Polyadenylic Acid, and Polyuridylic Acid as Homopolymers or as Segments Within Single RNA Molecules," Biophys. J., 77 3227-33 (1999), 7 pages.

Amit Meller et al., "Rapid nanopore discrimination between single polynucleotide molecules," PNAS, Feb. 1, 2000, vol. 97, No. 3, pp. 1079-1084.

Akeson, Mark, et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77, Dec. 1999, pp. 3227-3233.

Branton, Daniel, et al., "The potential and challenges of nanopore sequencing" NIH Public Access—Author Manuscript, Nat Biotechnol. available in PMC May 18, 2009, pp. 1-17.

Gracheva, Maria E. et al., "Simulation of the electric response of DNA translocation through a semiconductor nanopore—capacitor", Institute of Physics Publishing, Nanotechnology, vol. 17 (2006), pp. 622-633.

Heng, Jiunn B. et al., "Sizing DNA Using a Nanometer-Diameter Pore", Biophysical Journal, vol. 87, Oct. 2004, pp. 2905-2911.

Kasianowicz, John J., et al., "Characterization of individual polynucleotide molecules using a membrane channel", Proc. Natl. Acad. Sci. USA, vol. 93, Nov. 1996, pp. 13770-13773.

Lagerqvist, Johan et al., "Fast DNA Sequencing via Transverse Electronic Transport", Nano Lett., vol. 6, No. 4, Received Jan. 17, 2006; revised Manuscript Received Mar. 1, 2006, pp. 779-782.

Soni, Gautam V. et al., "Progress toward Ultrafast DNA Sequencing Using Solid-State Nanopores", Clinical Chemistry, vol. 53, No. 11, (2007), pp. 1-6.

Douville, et al., "DNA Linearization Through Confinement in Nanofluidic Channels, Anal Bioanal Chem.", Aug. 2008; vol. 391; No. 7; pp. 2395-2409; Abstract; p. 2402, col. 2; para 5; p. 2406; col. 2; para 2; p. 2407; Fig. 5b.

B. Luan et al., "Tribological Effects on DNA Translocation in a Nanochannel Coated with a Self-Assembled Monolayer," J. Phys. Chem. B, vol. 114, 2010, pp. 17172-17176; Nov. 12, 2010.

Bae, S. et al., "Roll-to-Roll Production of 30-inch Graphene Films for Transparent Electrodes," Nature Nanotechnology, Published online: Jun., 20, 2010, 5 pages.

Branton D, Deamer D W, Marziali A, Bayley H, Benner S A, Butler T, Di Ventra M, Garaj S, Hibbs A, Huang X, Jovanovich S B, Krstic P S, Lindsay S, Ling X S, Mastrangelo C H, Meller A, Oliver JS, Pershin YV, Ramsey JM, Riehn R, Soni GV, Tabard-Cossa V, Wanunu M, Wiggin M, Schloss J A, "The Potential and Challenges of

(56) References Cited

OTHER PUBLICATIONS

Nanopore Sequencing," Nature Biotechnology, Found online: http://www.nature.com/naturebiotechnology, 26(10) 1146-1153 (2008), 8 pages.

D. Branton et al., "The Potential and Challenges of DNA Sequencing," Nat. Biotech., vol. 26 (10), pp. 1146-1153 (2008).

I. Braslavsky, B. Hebert, E. Kartalov, S. R. Quake, "Sequence Information Can Be Obtained from Single DNA Molecules," Proc. Natl. Acad. Sci. USA, vol. 100, pp. 3960-3964 (2003).

F. S. Collins, M. Morgan, A. Patrinos, "The Human Genome Project—Lessons From Large-scale Biology," Science, vol. 300, pp. 286-290 (2003).

D. W. Hess, "Plasma-assisted oxidation, anodization, and nitridation of silicon," IBM J. Res. Develop. vol. 43. No. 1/2, Jan./Mar. 1999, pp. 127-145.

M. Fedurco, A. Romieu, S. Williams, I. Lawrence, G. Turcatti, "BTA, a Novel Reagent for DNA Attachment on Glass and Efficient Generation of Solid-phase Amplified DNA Colonies," Nucleic Acids Res. vol. 34, pp. e22 (2006).

A. K. Geim and K. S. Novoselov, "The Rise of Graphene," Nature Materials 6, 183 (2007), 9 pages.

Gracheva M E, Xiong A, Aksimentiev A, Schulten K, Timp G and Leburton J P, "Simulation of the Electric Response of DNA Translocation Through a Semiconductor Nanopore-capacitor," Nanotechnology, Published Jan. 6, 2006, Online: stacks.iop.org/Nano/17/622; 12 pages.

S. Harrer et al. "Electrochemical Characterization of Thin Film Electrodes Towards Developing a DNA-Transistor," Langmuir, vol. 26 (24), pp. 19191-19198 (2010).

S. Harrer et al., "Electrochemical Protection of Thin Film Electrodes in Solid State Nanopore," Nanotechnology, vol. 22, 2011, 275304, 6 pages.

T. D. Harris et al., "Single-molecule DNA Sequencing of a Viral Genome," Science, vol. 320, pp. 106-109 (2008).

J. Hass, W.A. De Heer and E.H. Conrad, "The Growth and Morphology of Epitaxial Multilayer Graphene," Journal of Physics: Condensed Matter 20, 323202 (2008), 28 pages.

Heng J B, Ho C, Kim T, Timp R, Aksimentiev A, Grinkova Y V, Sligar S, Schulten K and Timp G, "Sizing DNA Using a Nanometer-diameter Pore," Biophys Journal vol. 87, 2905-2911 (Oct. 2004); 7 pages.

H.W.C. Postma, "Rapid Sequencing of Individual DNA Molecules in Graphene Nanogaps," Nano Letters, vol. 10, No. 2, Jan. 4, 2010, pp. 420-425.

International Search Report—PCT; Notification of Transmittal of the International Search Report and the Written Opinion of the International Searching Authority, or the Declaration; Apr. 5, 2011; International application No. PCT/US1123872.

J. Prasongkit et al., "Transverse conductance of DNA necleotides in a graphene nanogap from first principles," arXiv:1012.1669v2 [physics.ins-det], [v1] Dec. 8, 2010, [v2] Jan. 14, 2011, Nano Lett., vol. 11, No. 5, 2011, pp. 1941-1945.

J. J. Kasianowicz, E. Brandin, D. Branton, D. W. Deamer, "Characterization of Individual Polynucleotide Molecules Using a Membrane Channel," Proc. Natl. Acad. Sci. USA., vol. 93, pp. 13770-13773 (1996).

K.S. Kim, Y. Zhao, H. Jang, S. Y. Lee, J. M. Kim, K. S. Kim, J. H. Ahn, P. Kim, J. Y. Choi, B. H. Hong, "Large-Scale Pattern Growth of Graphene Films for Stretchable Transparent Electrodes," Nature 457, 706-710 (2009).

Lagerqvist J, Zwolak M and Di Ventra M, "Fast DNA Sequencing Via Transverse Electronic Transport," Nano Lett. 6 779-782 (2006).

B. Luan, H. Peng, S. Polonsky, S. Rossnagel, G. Stolovitzky, and G. Martyna, "Base-by-base Ratcheting of Single-stranded DNA Through a Solid-state Nanopore," Phys. Rev. Lett., vol. 104 (23) pp. 238103-1-238103-4 (2010).

B. Luan, A. Aksimentiev, "Control and Reversal of the Electrophoretic Force on DNA in a Charged Nanopore," J. Phys. Condens. Matter, vol. 22, pp. 454123 (2010).

B. Luan et al., "Tribological Effects on Dna Translocation in a Nanochannel Coated with a Self-Assembled Monolayer," J. Phys. Chem. B, vol. 114, 2010, pp. 17172-17176.

M. J. Kim et al., "Rapid Fabrication of Uniformly Sized Nanopores and Nanopore Arrays for Parallel DNA Analysis," Adv. Mater. 2006, 18, pp. 3149-3153.

M. Margulies et al., "Genome Sequencing in Mircrofabricated High-density Pico-litre Reactors," Nature, vol. 437, pp. 376-380 (2005).

Meller A., Nivon L., Brandin E., Golovchenko J. and Branton D., "Rapid Nanopore Discrimination Between Signle Polynucleotide Molecules," Proc. Natl Acad. Sci. USA 97 1079-84 (2000).

United States Patent and Trademark Office, Non-Final Office Action for U.S. Appl. No. 12/704,665 received Mar. 16, 2011; pp. 1-15.

Novoselov K S et al, "Electric Field Effect in Atomically Thin Carbon Films" Science, American Association for the Advancement of Science, US, Washington, DC, vol. 306, No. 5696, Oct. 11, 2004, pp. 666-669, XP009086357, ISSN: 0036-8075, the whole document.

Fernando Patolsky, Gengfeng Zheng, Oliver Hayden, Melike Lakadamyali, Xiaowei Zhuang, and Charles M. Lieber, "Electrical detection of single viruses," Departments of Chemistry and Chemical Biology and Physics and Division of Engineering and Applied Sciences, Harvard University, Cambridge, MA 02138, Contributed by Charles M. Lieber, Aug. 20, 2004, pp. 1-6.

Polonsky et al., "Nanopore in metal-dielectric sandwich for DNA position control," Applied Physics Letters 91, 153103 (2007).

F. Sanger, S. Nicklen, A. R. Coulson, "DNA sequencing with chain termination inhibitors," Proc. Natl. Acad. Sci USA., vol. 74 (12), pp. 5463-5467 (1977).

He, et al., "Identification of DNA Basepairing via Tunnel-Current Decay," Nano Letters 2007; vol. 7, No. 12; pp. 3854-3858.

H. Stranneheim, et al., "Stepping Stones in DNA Sequencing," Biotechnical Journal (2012)7 (9) pp. 1063-1073.

\* cited by examiner

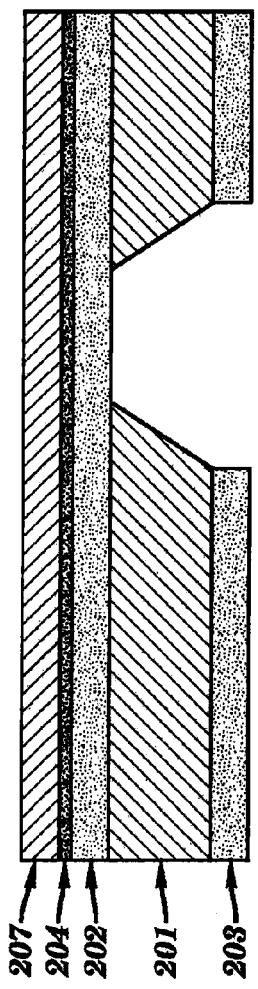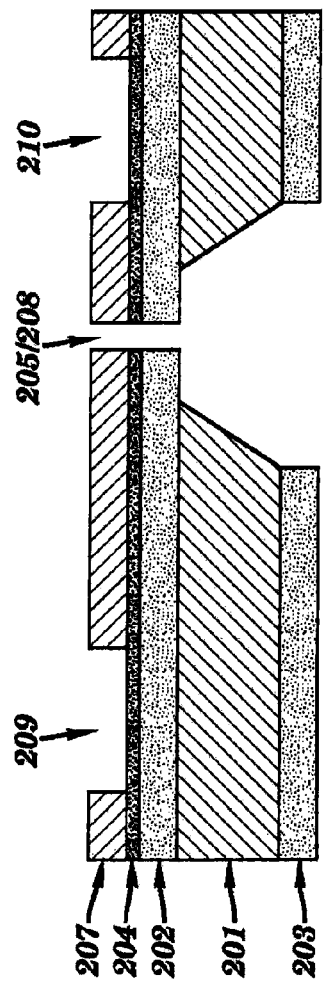

ELECTRON BEAM SCULPTING OF TUNNELING JUNCTION FOR NANOPORE DNA SEQUENCING

CROSS-REFERENCE TO RELATED APPLICATIONS AND PRIORITY CLAIM

This application is a continuation of U.S. Non-Provisional application Ser. No. 13/359,729, entitled "ELECTRON BEAM SCULPTING OF TUNNELING JUNCTION FOR NANOPORE DNA SEQUENCING", filed Jan. 27, 2012, which is based on and claims priority to U.S. Provisional Patent Application 61/437,102, entitled "ELECTRON BEAM SCULPTING OF TUNNELING JUNCTION FOR NANOPORE DNA SEQUENCING", filed Jan. 28, 2011, both of which are incorporated herein by reference in their entirety.

BACKGROUND

Exemplary embodiments relate to nanodevices, and more specifically to a tunneling junction and nanopore structure in a nanodevice Nanopore sequencing is a method for determining the order in which nucleotides occur on a strand of Deoxyribonucleic acid (DNA). A nanopore is a small hole on the order of several nanometers in internal diameter. The theory behind nanopore sequencing has to do with what occurs when the nanopore is immersed in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be put around the nanopore so that DNA bases can be differentiated while the DNA passes through the nanopore.

DNA could be driven through the nanopore by using various methods. For example, an electric field might attract the DNA towards the nanopore, and it might eventually pass through it. The scale of the nanopore means that the DNA may be forced through the hole as a long string, one base at a time, rather like thread through the eye of a needle.

BRIEF SUMMARY

According to an exemplary embodiment, a method of configuring a nanodevice is provided. The method includes filing a reservoir with a conductive fluid, configuring a membrane to separate the reservoir in the nanodevice, where the membrane includes an electrode layer having a tunneling junction formed therein. The method includes configuring the membrane to have a nanopore formed through other layers of the membrane such that the nanopore is aligned with the tunneling junction of the electrode layer. When a voltage is applied to the electrode layer, a tunneling current is generated by a base in the tunneling junction to be measured as a current signature for distinguishing the base. When an organic coating is formed on an inside surface of the tunneling junction, transient bonds are formed between the electrode layer and the base.

Other systems, methods, apparatus, design structures, and/or computer program products according to embodiments will be or become apparent to one with skill in the art upon review of the following drawings and detailed description. It is intended that all such additional systems, methods, apparatus, design structures, and/or computer program products be included within this description, be within the scope of the exemplary embodiments, and be protected by the accompanying claims. For a better understanding of the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features are apparent from the following detailed description taken in conjunction with the accompanying drawings in which:

FIG. 4A illustrates a schematic of the integration of a tunneling junction with a nanopore in accordance with an exemplary embodiment.

FIG. 4B illustrates a schematic continuing integration of a tunneling junction with a nanopore in accordance with an exemplary embodiment.

DETAILED DESCRIPTION

Exemplary embodiments provide an approach to make a nanometer size tunneling junction by focus electron beam cutting, and then to fine tune the junction size, by expanded electron beam techniques. Exemplary embodiments also include the integration of such tunneling junction with a nanopore for the purpose of DNA sequencing in a nanodevice.

Recently, there has been growing interest in applying nanopores as sensors for rapid analysis of biomolecules such as DNA, ribonucleic acid (RNA), protein, etc. Special emphasis has been given to applications of nanopores for DNA sequencing, as this technology is believed to hold the promise to reduce the cost of sequencing below $1000/human genome. One issue in nanopore DNA sequencing is electrically differencing individual DNA bases by leveraging this nanopore platform.

In accordance with exemplary embodiments, an approach is disclosed which uses a focused electron beam (e.g., utilizing a beam size as small as 0.4 nm) to cut a thin metal layer (shown as cut line 105 in FIG. 1A) to form the tunneling junction. Under a low intensity electron beam, material migration can occur, and the material migration can be used to fine tune the gap size of the tunneling junction. If the thin metal layer is on a free-standing membrane, one can also make the nanopore (shown as nanopore 206, 208 in FIGS. 2B-2I) through the top of the membrane at the gap to create the tunneling junction right at the entrance, at the inner surface, and/or the exit of the nanopore for DNA sequencing purposes via the tunneling current.

Figure 1A:
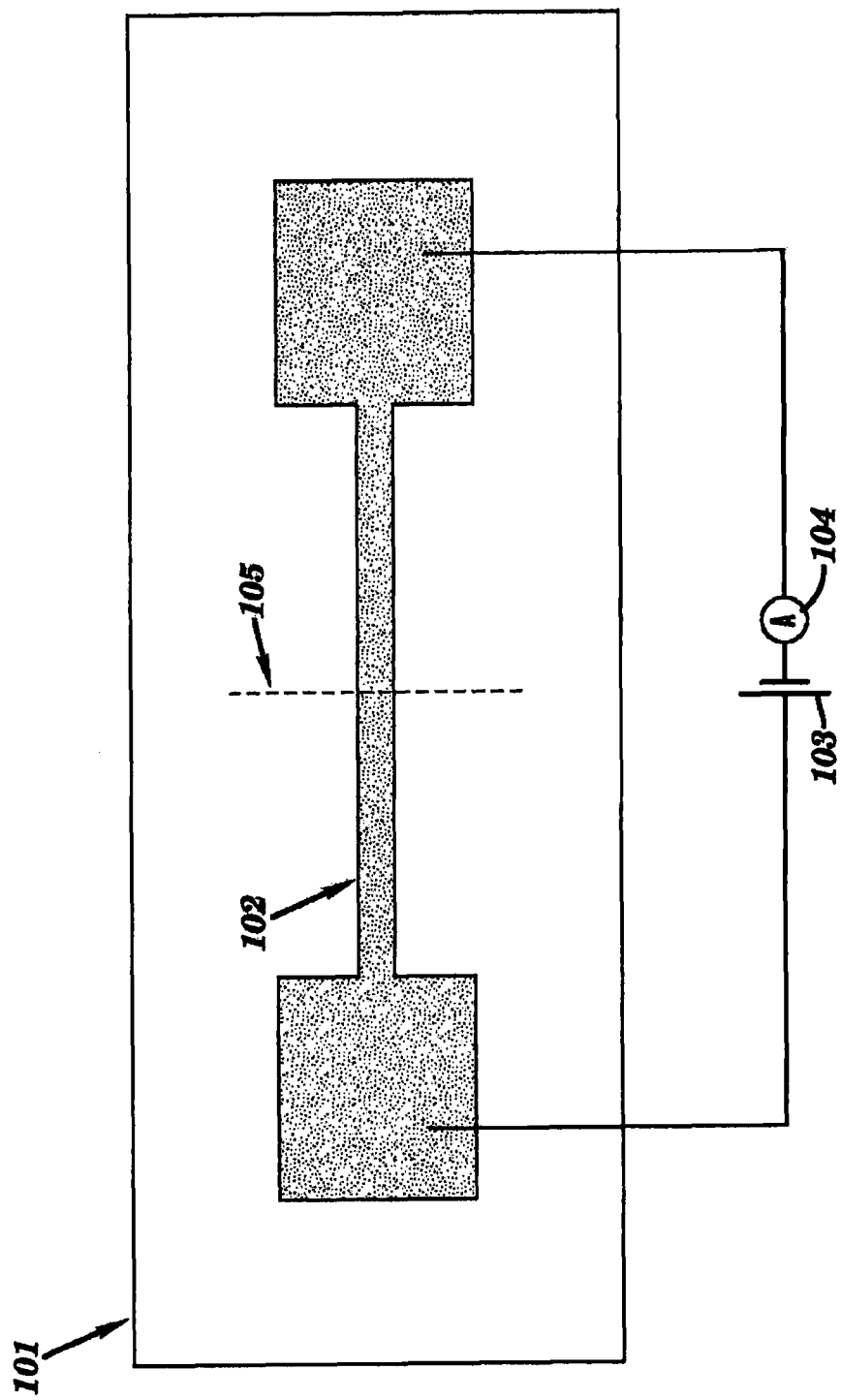
FIG. 1A illustrates a schematic of a process to make a tunneling junction by focused electron beam cutting and to fine tune the junction size by expanded electron beam in accordance with an exemplary embodiment.
Figure 1B:
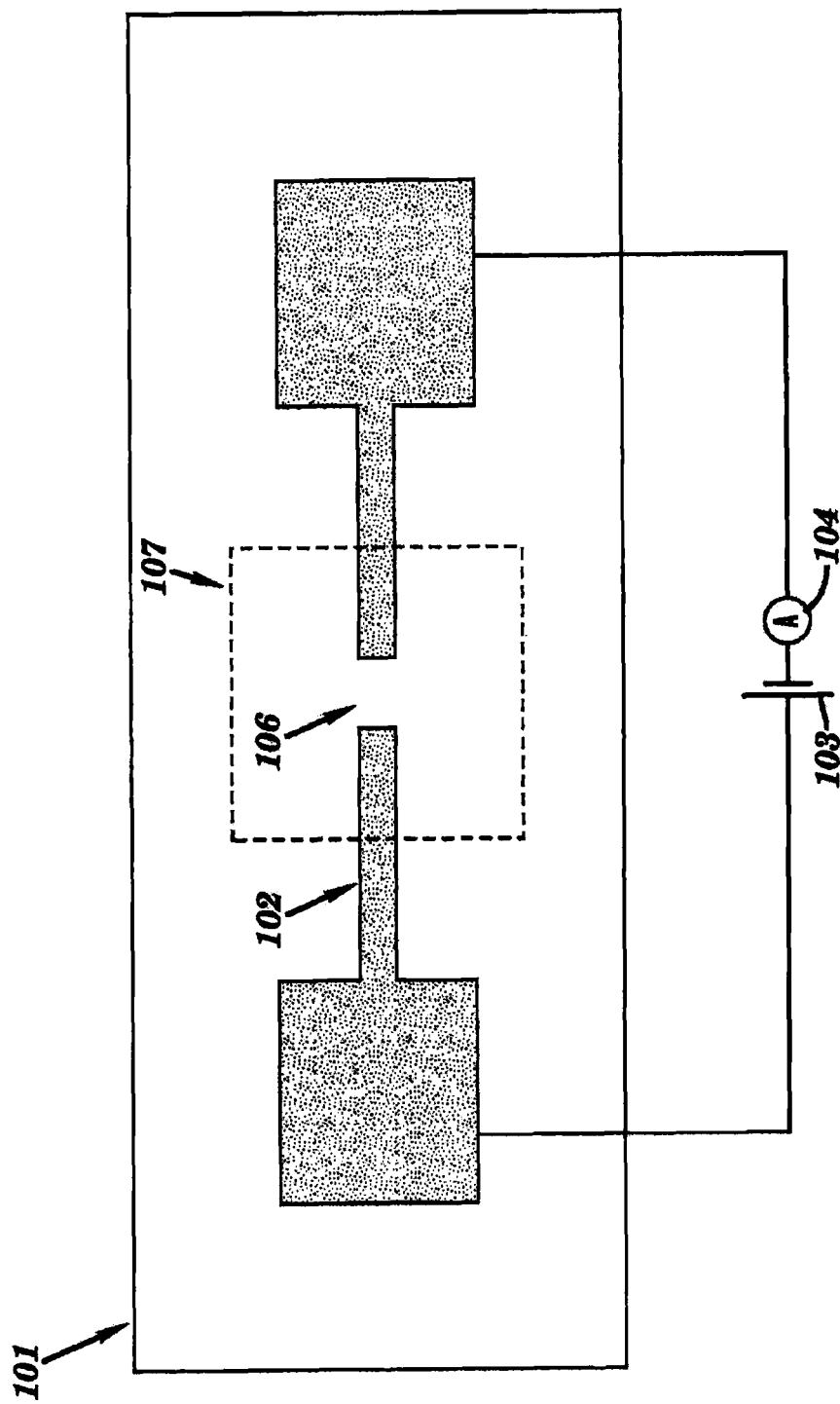
FIG. 1B illustrates a schematic continuing a process to make a tunneling junction in accordance with an exemplary embodiment.
Figure 1C:
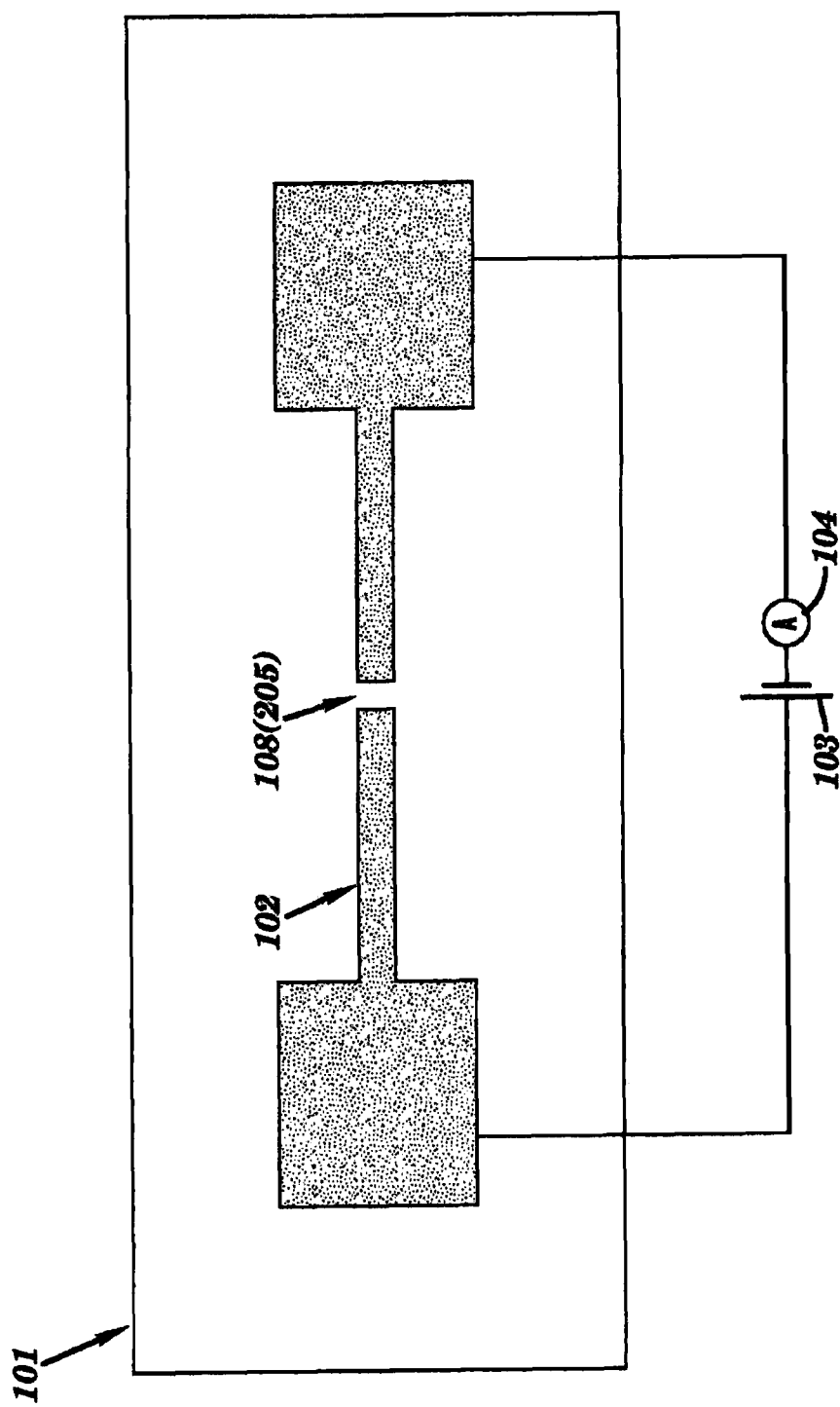
FIG. 1C illustrates a schematic continuing a process to make a tunneling junction in accordance with an exemplary embodiment.

Now turning to the figures, FIGS. 1A-1C illustrate a schematic of a process to make a tunneling junction by focused electron beam cutting and to fine tune the junction size by expanded electron beam according to an exemplary embodiment. FIGS. 1A-1C are top views of the schematic. In FIG. 1A, a substrate 101 can be any electrically insulating substrate, and layer 102 can be any electrically conductive layer such as a metal on top of the substrate 101. Voltage is applied by voltage source 103 between two ends of the conductive layer 102 and current is monitored through the ammeter 104. A focused electron beam (not shown) could be as small as 0.4 nm, and the focused electron beam performs line scanning shown as line 105 at the center location of conductive layer 102 (e.g., in a vacuum). One skilled in the art understands electron beam lithography (e-beam lithography), and understands the practice of scanning a beam of electrons in a patterned fashion across a surface.

The high energy, high density electron beam can sputter/etch material on its way into the vacuum gradually. When the voltage at voltage source 103 is being applied, the current measured by its corresponding ammeter 104 serves as a feedback that the current through ammeter 104 will drop down to zero (0) once the conductive layer 102 is cut into two halves by the electron beam, as shown in FIG. 1B. FIG. 1B shows a left half and right half of the conductive layer 102. In this way, one can create a tunneling junction 106 without damaging the underneath substrate 101. The tunneling junction 106 which is a nanosize gap between two electrically conductive parts corresponds to the line 105 previously shown in FIG. 1A.

In FIG. 1B, with an expanded (i.e., low intensity) electron beam covering area 107, the (metal) material in the conductive layer 102 can migrate and the gap size of the tunneling junction 106 can be tuned; that is the tunneling junction 106 can be reduced or increased in size to be the tunneling junction 108 shown in FIG. 1C.

For example, to achieve the desired size tunneling junction (gap) 108, a low intensity electron beam can be used to bombard the conductive layer 102 at the tunneling junction (gap) 108 (106 in FIG. 1B); this will cause the conductive layer 102 material to get softer and flow under surface tension. The low intensity electron beam can be utilized to cause the conductive layer 102 material to flow such that the tunneling junction (gap) 108 is widened and/or flow such that the tunneling junction (gap) 108 is narrowed. As seen by the decrease in size of the tunneling junction (gap) 106 in FIG. 1B to the tunneling junction (gap) 108 in FIG. 1C (which is not drawn to scale), material migration has caused the tunneling junction (gap) 106 to narrow. If the substrate 101 is a thin membrane, the whole tuning process can be monitored under a transmission electron microscope in real-time. Thus, one can acquire (tune) the exact size of the tunneling junction (gap) 108 by turning off the electron beam at the right moment. After fine tuning the tunneling junction 106, the tunneling junction 106 is now represented as the finely tuned tunneling junction (gap) 108 in FIG. 1C.

Figure 2A:
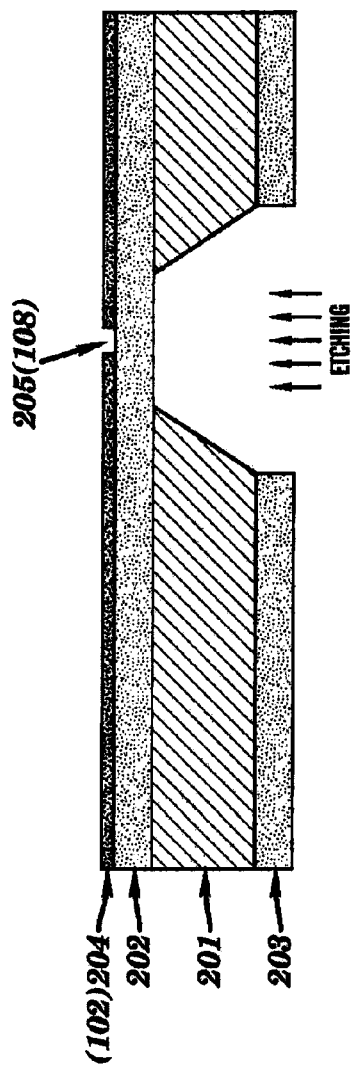
FIG. 2A illustrates a schematic of the integration of a tunneling junction with a nanopore in accordance with an exemplary embodiment.
Figure 2B:
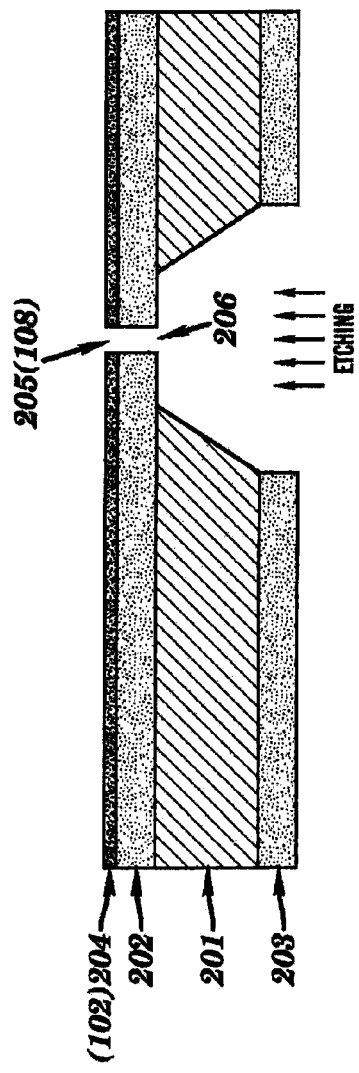
FIG. 2B illustrates a schematic continuing the integration of a tunneling junction with a nanopore in accordance with an exemplary embodiment.

FIGS. 2A-2F illustrate a schematic of the integration of the tunneling junction 108 with a nanopore in accordance with an exemplary embodiment. FIGS. 2A, 2B, 2D, and 2E (including 4A and 4B) are a cross-sectional view of the schematic, and FIGS. 2C and 2F (including 4C) are top views of the schematic. In FIG. 2A, the substrate 201 can be any substrate, such as Si (silicon). Layers 202 and 203 are electrically insulating films, such as $Si_3N_4$ (compound of silicon and nitrogen). The insulating layer 203 serves as an etching mask for etching thorough the substrate 201 via either dry or wet etching, and the etching stops on insulating layer 202. In this way, part of the insulating layer 202 will be a free-standing membrane. Conductive layer 204 (corresponding to conductive layer 102 in FIG. 1) is an electrically conductive layer, and tunneling junction 205 (corresponding to tunneling junction/gap 108 in FIG. 1) is the tunneling junction made in the free-standing membrane part of conductive layer 204 using the method described in FIG. 1. The tunneling junction 205 will be visible under a transmission electron microscope, and a nanometer size pore (nanopore) 206 can be made through the tunneling junction 205 and the underneath insulating layer 202, as shown in FIG. 2B. In this way, the tunneling junction 205 is integrated with the nanopore 206. As seen in FIG. 2B, the nanopore 206 is a hole through the insulating layer 202 while the tunneling junction 205 is a gap in the conductive layer (metal) 204.

Figure 2C:
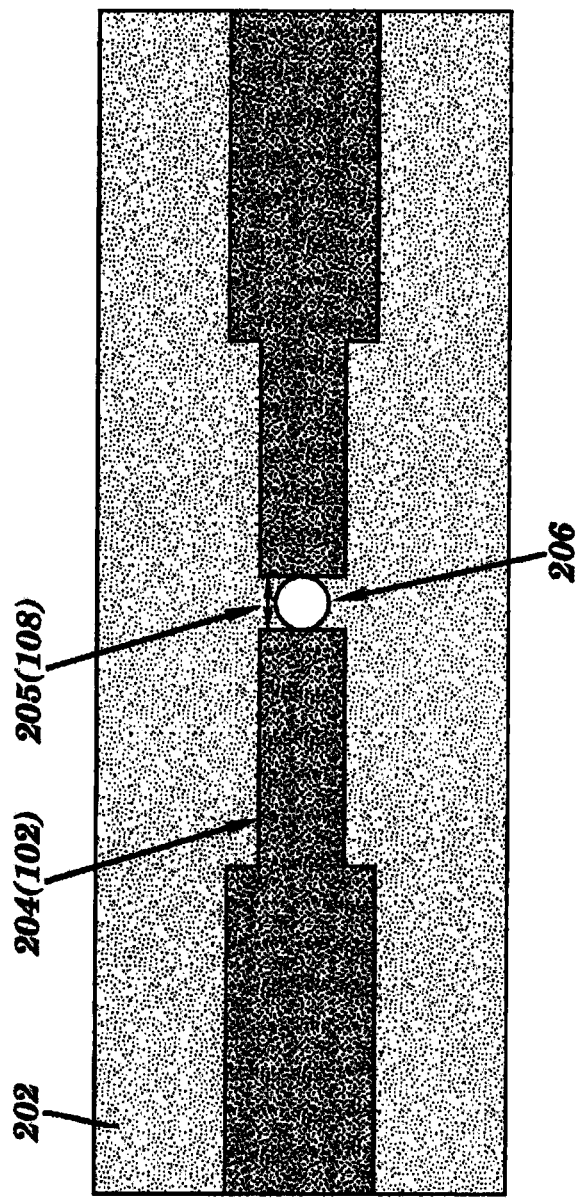
FIG. 2C illustrates a schematic continuing the integration of a tunneling junction with a nanopore in accordance with an exemplary embodiment.

FIG. 2C shows a top view of the schematic in FIG. 2B. As seen in the top view of FIG. 2C, the tunneling junction 205 (corresponding to tunneling junction/gap 108 in FIG. 1) is only between the conductive layer (metal) 204 (corresponding to conductive layer 102), and the tunneling junction 205 splits the conductive layer 204 into a left half and a right half. The nanopore 206 is formed through the tunneling junction 205 and goes through the substrate 201.

Figure 2D:
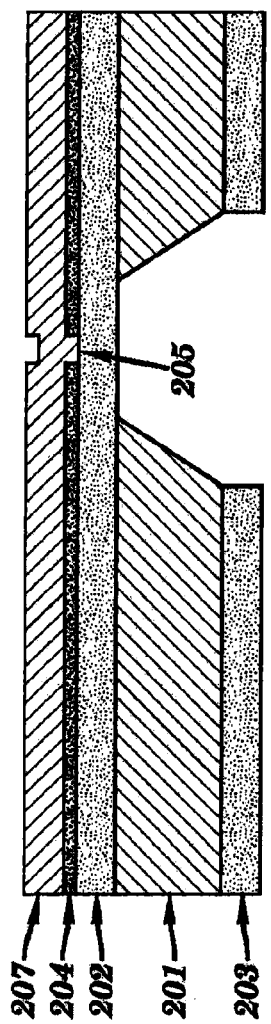
FIG. 2D illustrates a schematic continuing the integration of a tunneling junction with a nanopore in accordance with an exemplary embodiment.
Figure 2E:
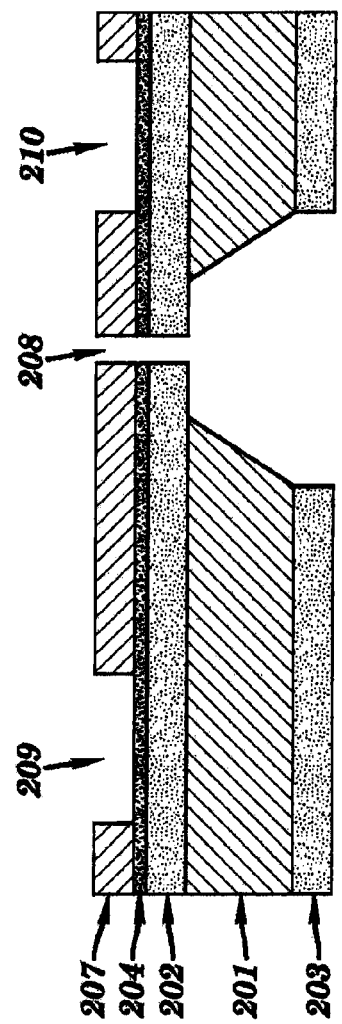
FIG. 2E illustrates a schematic continuing the integration of a tunneling junction with a nanopore in accordance with an exemplary embodiment.

In order to work with an electrically conductive solution, an insulating (cap) layer 207 (also called the passivation layer which may be a layer of oxide and/or silicon nitride) is deposited on the conductive layer 204, as shown in FIG. 2D (e.g., right after the tunneling junction 205 is made). The tunneling junction 205 will be visible under a transmission electron microscope and a nanometer size pore (nanopore) 208 can be made through the tunneling junction 205 and the underneath insulating layer 202, as shown in FIG. 2E. In this way, the tunneling junction 205 is embedded in the nanopore 208. The nanopore 206 may now be considered part of the nanopore 208. Via windows 209 and 210 are opened through the insulating layer 207 down to the conductive layer 204, for electrically accessing the two sides of the tunneling junction 205. The windows 209 and 210 will be used as electrodes/connections for connecting, e.g., a wire to the left and right halves of the conductive layer 204.

Figure 2F:
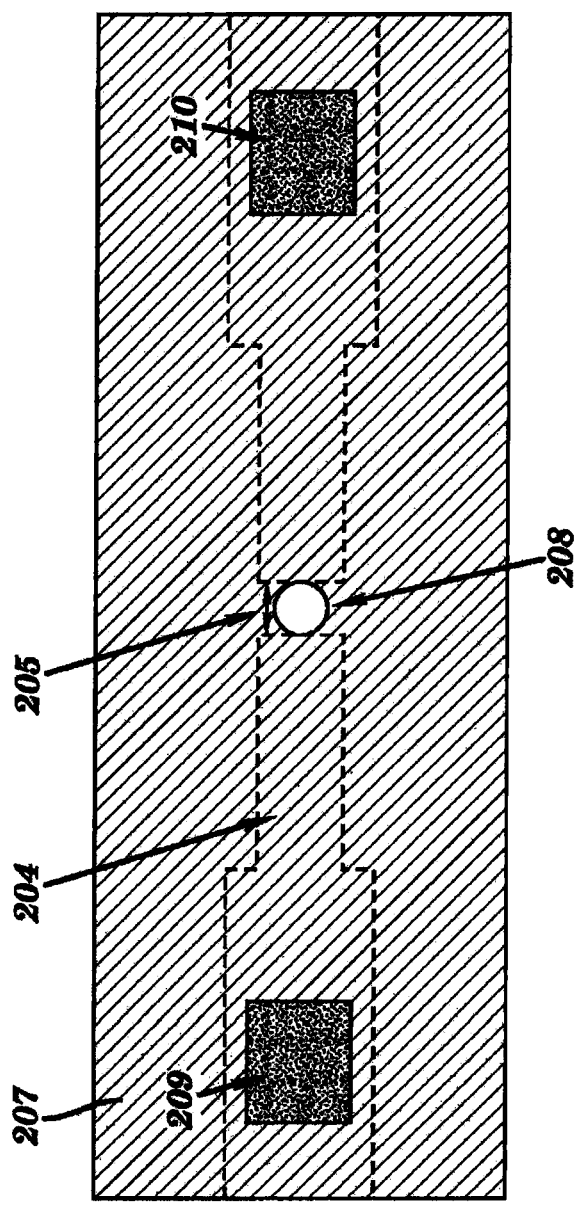
FIG. 2F illustrates a schematic continuing the integration of a tunneling junction with a nanopore in accordance with an exemplary embodiment.

FIG. 2F illustrates the top view of FIG. 2E. In FIG. 2F, the conductive layer 204 (shown as an outline with a dotted line) is buried underneath the insulation (passivation) layer 207 with windows 209 and 210 of the conductive layer 204 exposed. Although not visible in FIG. 2F, the nanopore 208 goes through the insulating layer 202 and the insulation (passivation) layer 207.

Figure 4C:
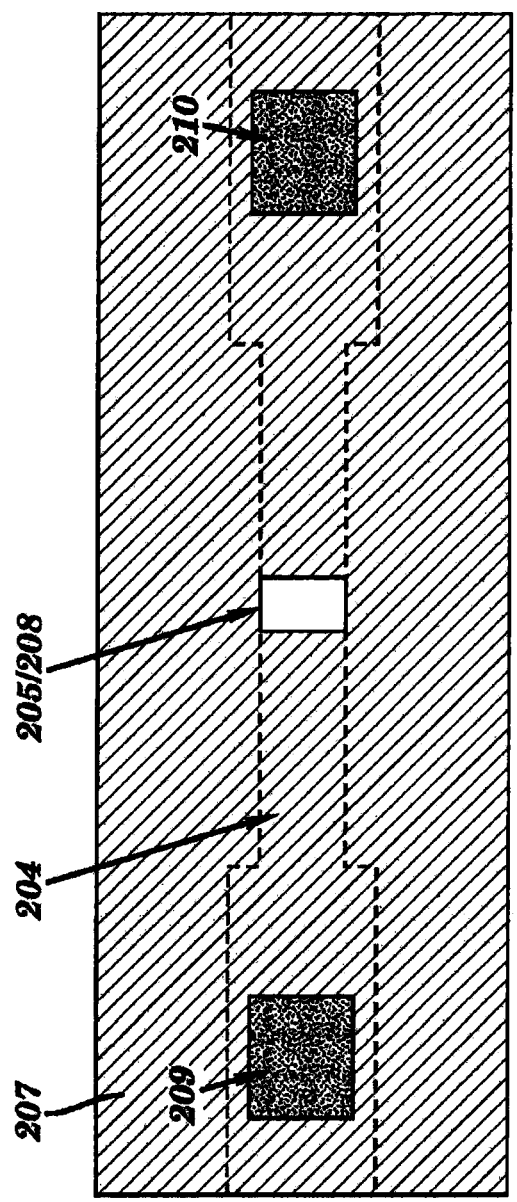
FIG. 4C illustrates a schematic continuing the integration of a tunneling junction with a nanopore in accordance with an exemplary embodiment.

FIGS. 4A, 4B, and 4C illustrate a variation of FIGS. 2A-2F in which the nanopore 208 and tunneling junction are made in the same electron beam cutting process and have the same shape in accordance with an exemplary embodiment. An insulating (cap) layer 207 (also called the passivation layer which may be a layer of oxide and/or silicon nitride) is deposited on the conductive layer 204, as shown in FIG. 4A. A focused electron beam is used to cut through all layers 207, 204, and 202 at the freestanding membrane part and to cut conductive layer 204 into two halves, as shown in FIG. 4B. In this way, the tunneling junction 205 and the nanopore 208 have exactly the same shape. Via windows 209 and 210 are opened through the insulating layer 207 down to the conductive layer 204, for electrically accessing the two sides of the tunneling junction 205. The windows 209 and 210 will be used as electrodes/connections for connecting, e.g., a wire to the left and right halves of the conductive layer 204.

FIG. 4C illustrates the top view of FIG. 4B. In FIG. 4C, the conductive layer 204 (shown as a dotted line) is buried underneath the insulating (passivation) layer 207 with windows 209 and 210 of the conductive layer 204 exposed. Although not visible in FIG. 4C, the nanopore 208 goes through the insulating layer 202 and the insulating (passivation) layer 207.

Figure 3A:
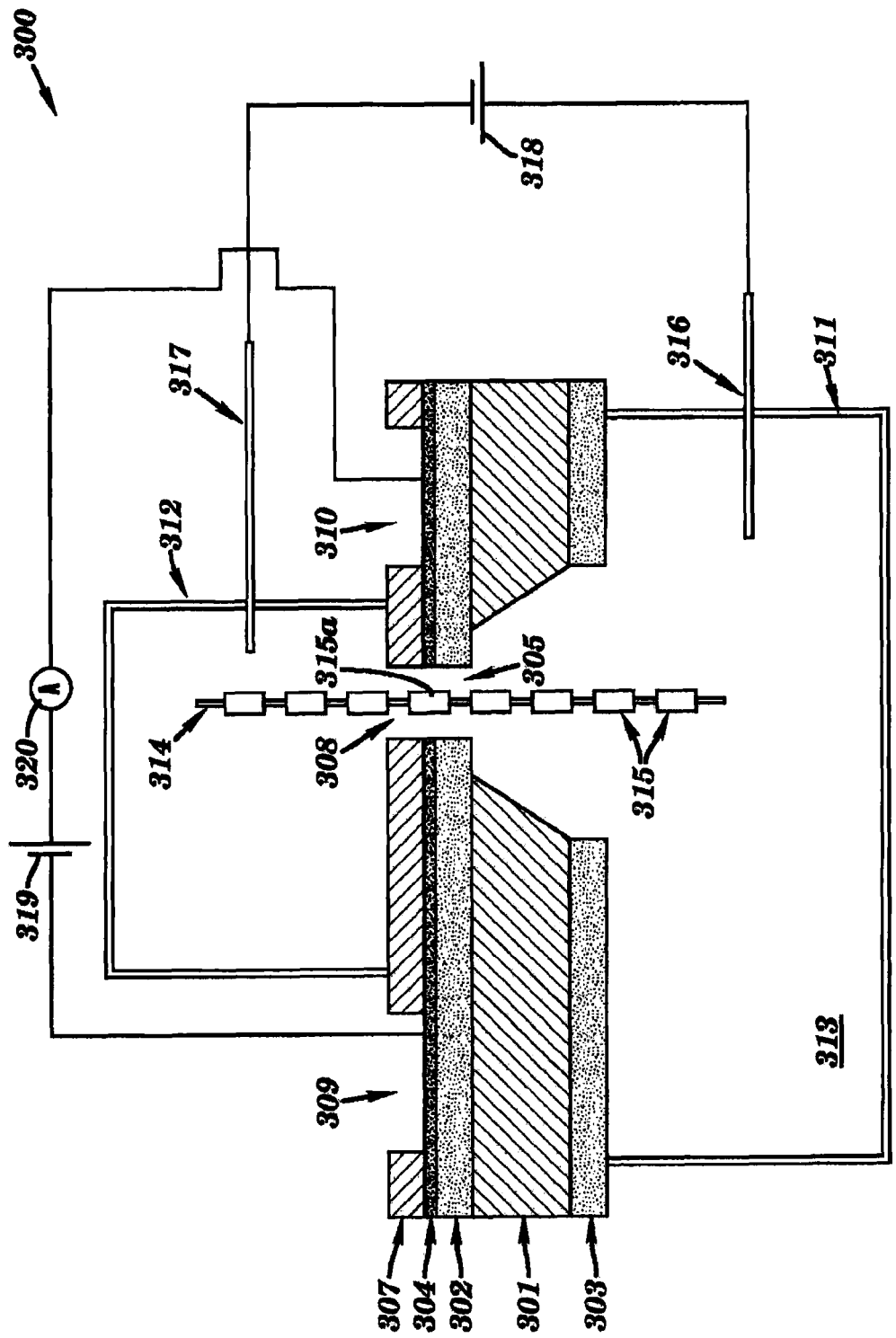
FIG. 3A illustrates a schematic of a tunneling junction nanopore device for DNA sequencing in accordance with an exemplary embodiment.
Figure 3B:
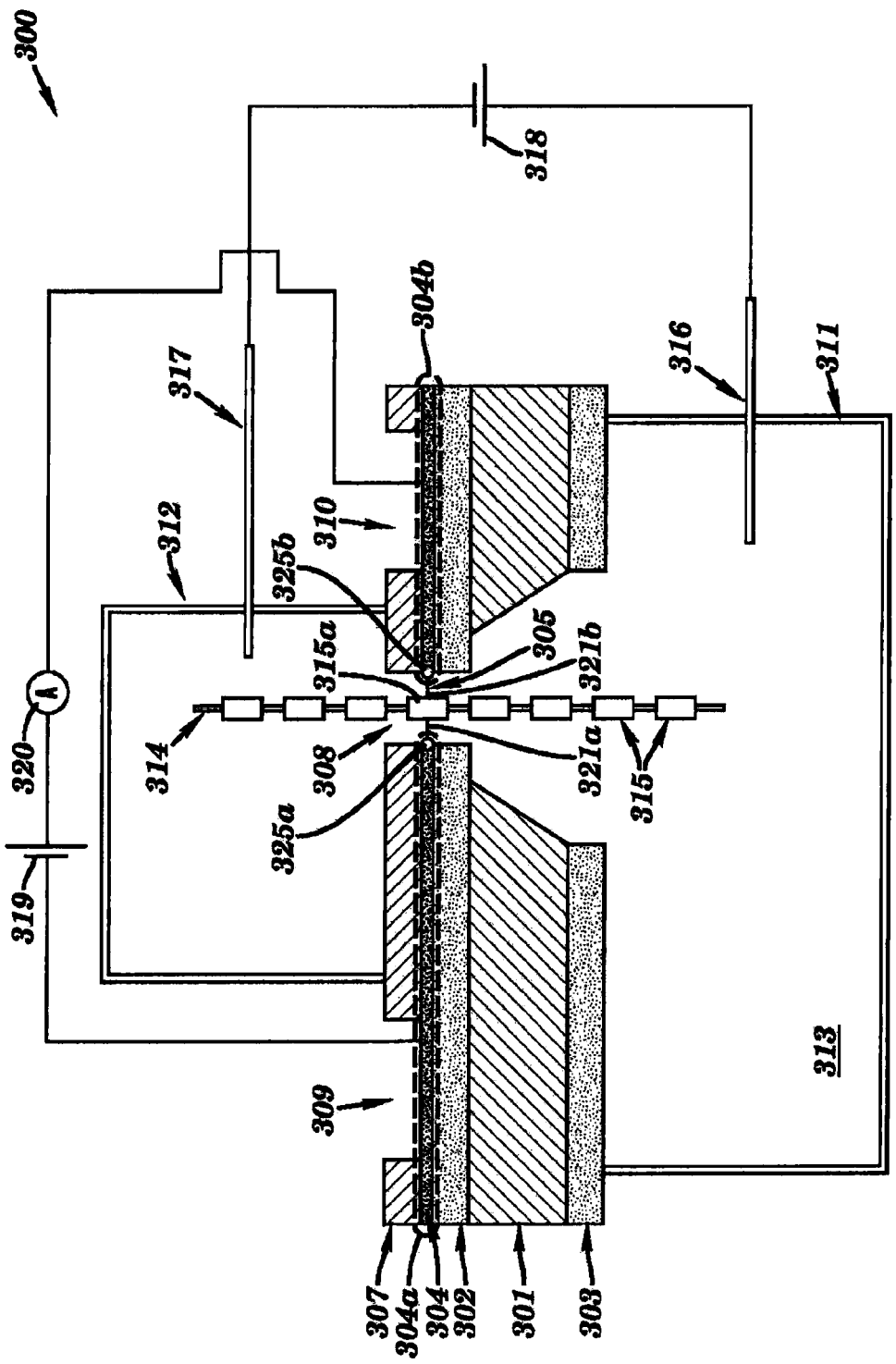
FIG. 3B illustrates a schematic of a tunneling junction nanopore device for DNA sequencing with an organic coating in accordance with an exemplary embodiment.

FIGS. 3A and 3B illustrate a schematic (system) of a tunneling junction (e.g., tunneling junction 106, 108, and 205) and nanopore device 300 for DNA sequencing according to an exemplary embodiment. FIGS. 3A and 3B show a cross-sectional view of the tunneling junction and nanopore device 300.

In FIGS. 3A and 3B, elements 301-310 are the same as elements 201-210 respectively. However, FIG. 3B includes an organic coating as discussed herein. The tunneling junction and nanopore device 300 partitions two reservoirs 311 and 312. Electrically conductive solution 313 fills the two reservoirs 311 and 312 as well as the nanopore 308. A negatively charged DNA 314 (with each base illustrated as base 315) can be driven into the nanopore 308 by a voltage of the voltage source 318 applied between the two reservoirs 311 and 312 via two electrodes 316 and 317, respectively. Voltage of the voltage source 319 is applied between the two sides (at left window 309 and right window 310) of the tunneling junction 305, and a baseline tunneling current is monitored at ammeter 320. The baseline tunneling current may be stored in memory 15 of a computer 600 (shown in FIG. 6) for further use as discussed herein. As DNA bases 315 pass through the tunneling junction 305 (which is the gap in the conductive (metal) layer 304), each of the DNA bases 315 can be identified by its respective tunneling current signal at the ammeter 320.

For example, voltage source 318 is turned on to drive the DNA 314 into the tunneling junction 305 which is the gap separating the conductive layer 304 into two halves. When, e.g., a base 315a is in the tunneling junction 305, voltage source 319 is turned on (while voltage source 318 is turned off) to measure the tunneling current of the base 315a. For instance, with voltage applied by voltage source 319, current flows through window 309 (acting as an electrode) of conductive layer 304, through the conductive layer 304, into the conductive solution (liquid) 313, into the DNA base 315a (which produces the tunneling current signature), out through the conductive solution 313, into the right side of the conductive layer 304, out through the window 310 (acting as an electrode), and into the ammeter 320 for measurement. The ammeter 320 may be implemented by and/or integrated in the computer 600 (test equipment) for measuring the baseline tunneling current and tunneling current generated by the DNA base 315a. A software application 605 of the computer 600 is configured to measure, display, plot/graph, analyze, and/or record the measured tunneling current for each DNA base 315 that is tested. In the example above, the software application 605 (and/or a user utilizing the software application 605) can compare the baseline tunneling current measured with no DNA base 315 in the tunneling junction 305 to the tunneling current corresponding to each DNA base 315 (at a time) that is measured in tunneling junction 305. In the example, the tunneling current (signal) for the DNA base 315a is compared against the baseline tunneling current by the software application 605 (or a user utilizing the software application 605). The tunneling current (signature) for the DNA base 315a may have particular characteristics that are different from the baseline tunneling current measured by the ammeter 320, and the tunneling current (signatures) for the DNA base 315a can be utilized to identify and/or differentiate the DNA base 315a from other DNA bases 315 on the DNA 314.

For example, the measured tunneling current signature for DNA base 315a may have a positive pulse, a negative pulse, a higher or lower current (magnitude), an inverse relationship, a rising or falling plot, a particular frequency, and/or any other difference from the baseline tunneling current that can be determined by the software application 605 (and/or a user viewing the display 45 of the two different plots). This unique tunneling current signature can be utilized (by the software application 605) to distinguish the DNA base 315a from other DNA bases 315. Note that, the tunneling current measured at ammeter 320 between electrode layers does not require any electrical wiring between the left and right parts (which will be shown as electrodes 304a and 304b in FIG. 3B) of the conductive (electrode) layers 304 as electrons simply move from one electrode to the other in a quantum mechanical way. For example, there will be a baseline tunneling current when DNA base 315a is away (e.g., with distance much longer than the wavelength of an electron) from the tunneling junction 305. When DNA base 315a is close (e.g., within the distance of the wavelength of an electron) to the tunneling junction 305, the tunneling path of the electron will be rerouted to tunnel from the left part of the conductive (electrode) layer 304 to the DNA base 315a and then to the right part of the conductive (electrode) layer 304. In this way, the tunneling current (electrons) through the DNA base 315a will create a current signature (such as an increase of tunneling current, typically in the order of tens of pA (picoamperes)) added onto the baseline tunneling current trace. The tunneling current across DNA bases is dependent on the electronic and chemical structure of the DNA bases; thus, a different DNA base will generate a different tunneling current signature. If the difference between the tunneling current signatures of different bases is small or stochastic, repeating measurements on the same DNA base can be done; a histogram of the amplitudes of the tunneling current signatures can be fit and the statistical data will provide enough resolution to differentiate DNA bases.

FIG. 3B utilizes the approach discussed for FIG. 3A except that the conductive layer 304 is coated with organic coating 325a and 325b, which can form transient bonds 321a and 321b (such as a hydrogen bond (i.e., transient bonds 321) with the DNA base 315). In FIG. 3B, these transient bonds 321 formed by the organic coating 325a and 325b will fix the orientation of the DNA base 315 and the relative distance of the DNA base 315 to the conductive layer 304, for improving the tunneling current signal measured by ammeter 320 and for better identifying DNA bases 315. If the organic coating 325a and 325b and/or transient bonds 321a and 321b are electrically conductive, they will help to shrink the tunneling gap size and enhance the tunneling current signatures too. Also, the transient bonds 321a and 321b by the organic coating 325a and 325b hold the DNA 314 in place against thermal motion when measuring the tunneling current of the base 315. The forces of thermal motion may cause the DNA 314 to move, but the transient bonds 321a and 321b fix the base 315 in the tunneling junction 305 against the DNA movement caused by thermal motion.

Figure 5:
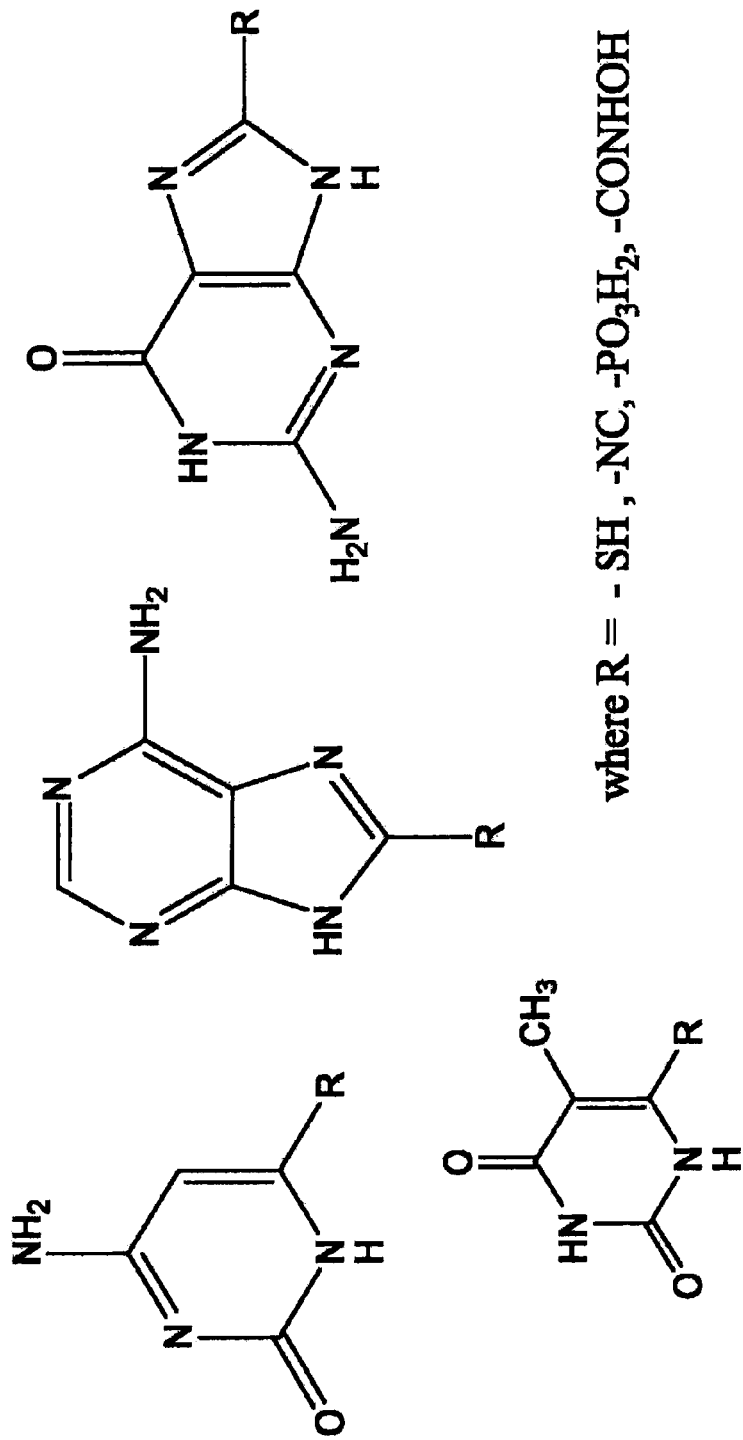
FIG. 5 illustrates examples of molecules for self-assembly inside nanopores in accordance with an exemplary embodiment.

In one implementation, the organic coating 325a and 325b consists of bifunctional small molecules which at one end form covalent bonds with conductive layer 304, and at the other end (of the organic coating 325a/b) which is exposed in the nanopore 308, the organic coating 325a and 325b consists of functionalities which can form strong hydrogen bonds with DNA and/or can protonate nucleotides to form acid base interactions. If the conductive layer 304 is made of metals such as gold, palladium, platinum etc., the first functionality which bonds to the conductive layer 304 can be chosen as thiols, isocyanides, and/or diazonium salts. If the conductive layer 304 is made of titanium nitrides or indium tin oxide (ITO), the covalent bonding functionality is chosen from phosphonic acid, hydroxamic acid, and/or resorcinol functionality. The small bifunctional molecules are designed in such a way that any charge formation due to interaction with DNA can easily be transferred to the conductive layer 304 and therefore a pi-conjugated moiety (e.g., benzene, diphenyl, etc.) are sandwiched between two functionalities. The second functionality is a group which can form a strong hydrogen bond with DNA. Examples of such groups include but are not limited to alcohols, carboxylic acids, carboxamides, sulfonamides, and/or sulfonic acids. Other groups which can be used to form interactions with DNA are individual self-assembled nucleotides. For example, adenine monophosphonic acid, guanine monophosphonic acid, etc., can be self-assembled on titanium nitride electrodes or mercapto thymine or mercapto cytosine self-assembles on metal electrodes such as gold and/or platinum. FIG. 5 illustrates examples of molecules for self-assembly inside nanopores according to exemplary embodiments. The molecules may be utilized as the organic coating 325a and 325b.

Referring to FIG. 3B, as discussed above, the voltage source 318 is applied to move the DNA 314 into the nanopore 308. When voltage of the voltage source 319 is applied (and the voltage source 318 is turned off), current flows through left electrode 304a, into the organic coating 325a, into the transient bond 321a (which acts as or can be thought of as a wire), into the DNA base 315a (producing the tunneling current), out through the transient bond 321b, out through the organic coating 325b, out through the right electrode 304b, and into the ammeter 320 to measure the tunneling current of the DNA base 315a. The ammeter 320 may be integrated with the computer 600, and the computer 600 can display on display 45 the tunneling current of the DNA base 315a versus the baseline tunneling current measured when no base 315 is in the tunneling junction 305.

Figure 7:
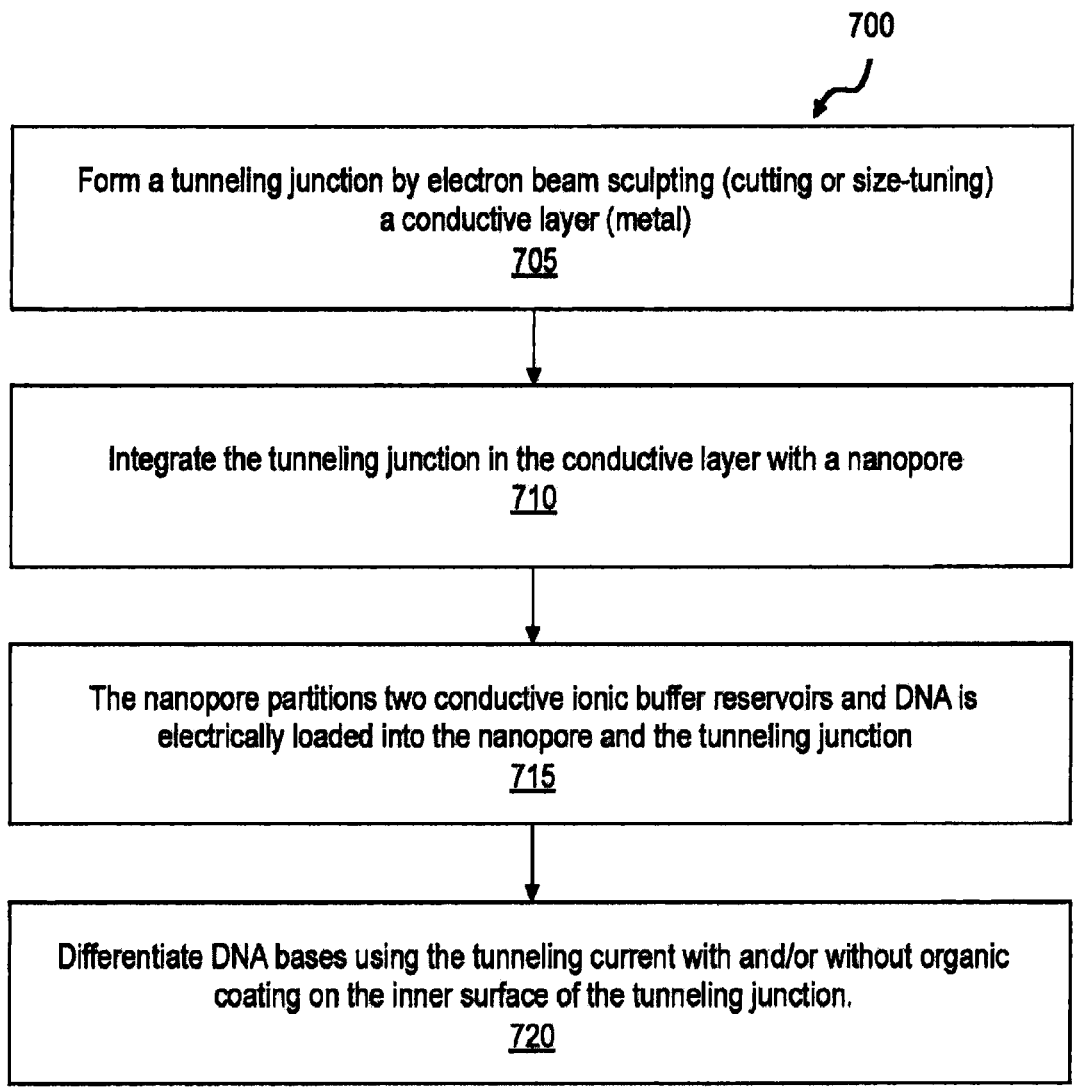
FIG. 7 illustrates a flow chart according to an exemplary embodiment.

FIG. 7 illustrates a method 700 according to exemplary embodiments, and reference can be made to FIGS. 1, 2, and 3.

At operation 705, a tunneling junction 108, 205, 305 is made by electron beam sculpting (cutting or size-tuning). Using a low intensity electron beam, the tunneling junction 108, 205, 305 can be widened by causing the material (metal) of the conductive layer 102, 204, 304 to migrate away from the tunneling junction gap, thus making the gap wider; similarly, using a low intensity electron beam spread across area 107 in FIG. 1, the tunneling junction 108, 205, 305 can be narrowed to cause the material of the conductive layer 102, 204, 304 to flow toward (into) the tunneling junction gap thus make the gap smaller.

At operation 710, the tunneling junction 108, 205 is integrated with a nanopore 208 as shown in FIGS. 2B-2F. The integrated (combined) tunneling junction 205 and nanopore 208 form a hole through multiple layers 207, 204, and 202 as shown in FIG. 2E. The distinction between the tunneling junction 205 and the nanopore 208 can be seen in FIG. 2F. This distinction is carried through to the tunneling junction 305 shown in FIG. 3 in which the tunneling junction 305 is the gap between the conductive layer 304 (i.e., separating the conductive layer 304 into two halves) but not layers 307, 302, 301, and 303. In one implementation, the tunneling junction 108, 205 is formed prior to forming the nanopore 208 (and/or nanopore 206).

At operation 715, the nanopore 208 partitions two conductive ionic buffer reservoirs 312 and 313, and the DNA 314 is electrically loaded into the nanopore 308 and the tunneling junction 305. The tunneling junction 305 is between the left half 304a and right half 304b of the conductive layer 304. The left and right halves 304a and 304b serve as electrodes for accessing the tunneling junction 305 (and the base 315 therein) by the voltage source 319 to measure the tunneling current with ammeter 320.

At operation 720, the DNA bases 315 are differentiated using the tunneling current of each individual base 315 (measured by ammeter 320) with and/or without organic coating 325a and 325b on the inside surface of the tunneling junction 305. The computer 600 can measure, analyze, differentiate, display, and record/store (in memory 15) the different tunneling currents measured for the different bases 315 of the DNA 314. The tunneling current measurements of the bases 315 with the organic coating 325a and 325b causing the transient bonds 321a and 321b would be different from the tunneling currents measurements of the same bases 315 without the organic coating 325a and 325b and without the transient bonds. For example, the tunneling current measured for base 315a with the organic coating 325a and 325b (causing transient bonds 321a and 321b) may have a greater magnitude than without the organic coating 325a and 325b.

Figure 6:
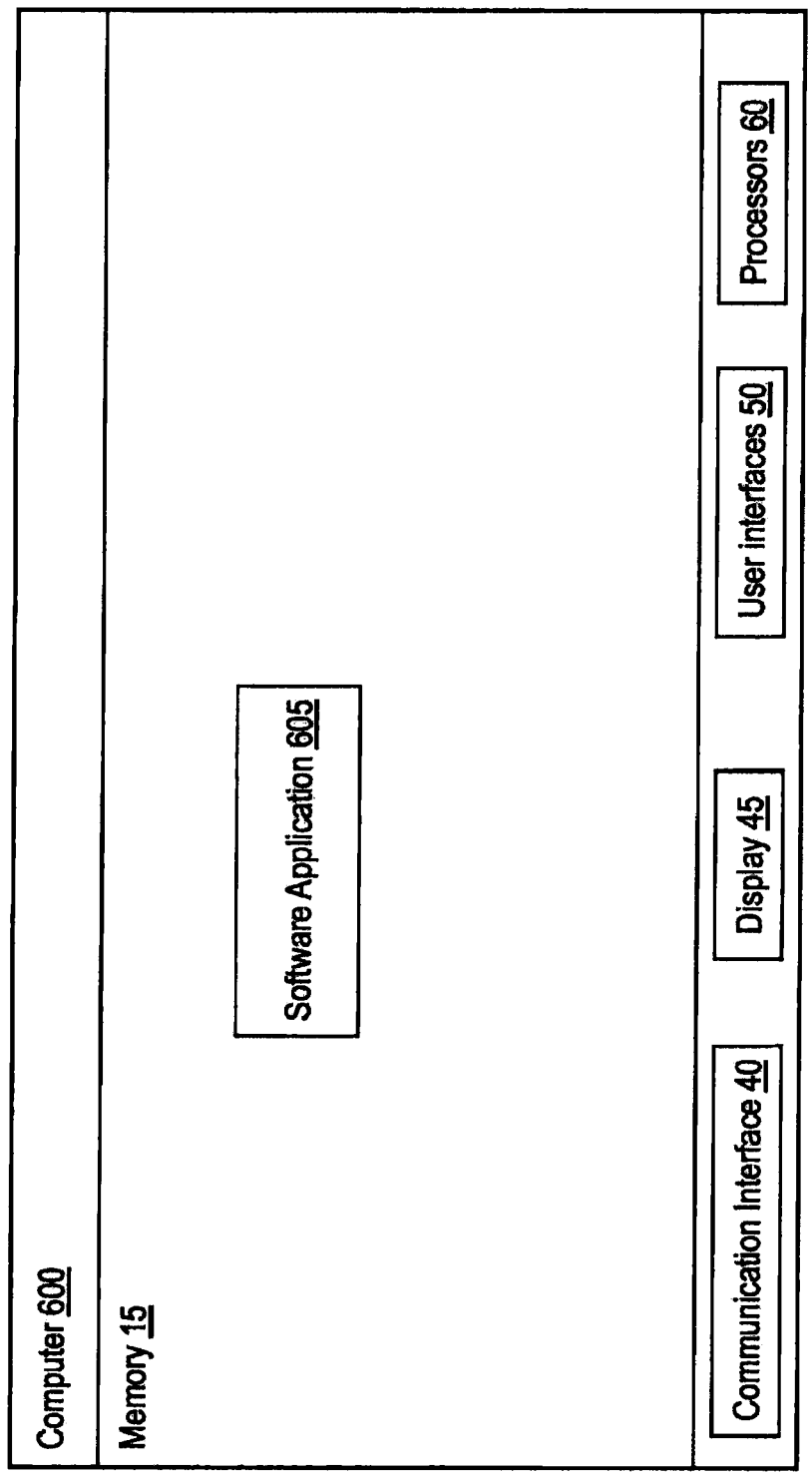
FIG. 6 illustrates a computer utilized according to exemplary embodiments.

Now turning to FIG. 6, FIG. 6 illustrates a block diagram of the computer 600 having various software and hardware elements for implementing exemplary embodiments. The computer 600 may be utilized in conjunction with any elements discussed herein.

The diagram depicts the computer 600 which may be any type of computing device and/or test equipment (including ammeters, voltage sources, connectors, etc.). The computer 600 may include and/or be coupled to memory 15, a communication interface 40, display 45, user interfaces 50, processors 60, and software 605. The communication interface 40 comprises hardware and software for communicating over a network and connecting (via cables, plugs, wires, electrodes, etc.) to the nanodevices discussed herein. Also, the communication interface 40 comprises hardware and software for communicating with, operatively connecting to, reading, and controlling voltage sources, ammeters, tunneling currents, etc., as discussed herein. The user interfaces 50 may include, e.g., a track ball, mouse, pointing device, keyboard, touch screen, etc, for interacting with the computer 600, such as inputting information, making selections, independently controlling different voltages sources, and/or displaying, viewing and recording tunneling current signatures for each base, etc.

The computer 600 includes memory 15 which may be a computer readable storage medium. One or more applications such as the software application 605 (e.g., a software tool) may reside on or be coupled to the memory 15, and the software application 605 comprises logic and software components to operate and function in accordance with exemplary embodiments in the form of computer executable instructions. The software application 605 may include a graphical user interface (GUI) which the user can view and interact with according to exemplary embodiments.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. A method of configuring a nanodevice, the method comprising:
    filing a reservoir with a conductive fluid;
    configuring a membrane to separate the reservoir in the nanodevice, the membrane comprising an electrode layer having a tunneling junction formed therein; and
    configuring the membrane to have a nanopore formed through other layers of the membrane such that the nanopore is aligned with the tunneling junction of the electrode layer;
    wherein when a voltage is applied to the electrode layer, a tunneling current is generated by a base in the tunneling junction to be measured as a current signature for distinguishing the base;
    wherein when an organic coating is formed on an inside surface of the tunneling junction, transient bonds are formed between the electrode layer and the base; and
    wherein the organic coating includes a selection from hydroxamic acid, resorcinol functionality, adnine monophosphonic acid, guanine monophosphonic acid, sulfonamides, and sulfonic acid.

2. The method of claim 1, wherein the tunneling junction is cut into the electrode layer by a focused electron beam.

3. The method of claim 1, wherein a first insulating layer is underneath a substrate and a second insulating layer is above the substrate; and
    wherein the electrode layer having the tunneling junction is above the second insulating layer.

4. The method of claim 3, wherein a third insulating layer is above the electrode layer; and
    wherein the second insulating layer and the third insulating layer are the other layers through which the nanopore is formed.

5. The method of claim 4, wherein the nanopore formed through the second insulating layer and the third insulating layer is aligned to the tunneling junction in the electrode layer.

6. The method of claim 1, wherein the transient bonds hold the base in place against thermal motion.

7. The method of claim 1, wherein the transient bonds improve the current signature of the base.

* * * * *